United States Patent [19]

Atkinson et al.

[11] Patent Number: 4,545,909
[45] Date of Patent: * Oct. 8, 1985

[54] GROWTH OF BIOMASS

[75] Inventors: Bernard Atkinson, Copthorne; Geoffrey M. Black, Sale; Anthony Pinches, Offerton; Paul J. S. Lewis, Abbotts Langley, all of England

[73] Assignees: The University of Manchester Institute of Science and Technology; Simon-Hartley Limited, both of Manchester, England

[*] Notice: The portion of the term of this patent subsequent to Dec. 6, 2000 has been disclaimed.

[21] Appl. No.: 557,318

[22] Filed: Dec. 2, 1983

Related U.S. Application Data

[60] Continuation of Ser. No. 347,872, Feb. 11, 1982, Pat. No. 4,419,243, which is a continuation-in-part of Ser. No. 156,038, Jun. 3, 1980, abandoned, which is a division of Ser. No. 945,869, Sep. 26, 1978, abandoned.

[30] Foreign Application Priority Data

Oct. 20, 1977 [GB] United Kingdom ............... 43613/77
Oct. 20, 1977 [GB] United Kingdom ............... 43614/77
Oct. 20, 1977 [GB] United Kingdom ............... 43615/77

[51] Int. Cl.$^4$ .................................................. C02F 3/08
[52] U.S. Cl. ..................................... 210/618; 435/285
[58] Field of Search ................. 210/615–618, 210/150, 151; 435/285

[56] References Cited

U.S. PATENT DOCUMENTS

| 3,855,120 | 12/1974 | Garbo | 210/618 |
| 4,005,010 | 1/1977 | Lunt | 210/615 |
| 4,009,098 | 2/1977 | Teris | 210/618 |
| 4,055,490 | 10/1977 | Hasegawa et al. | 210/616 |
| 4,165,281 | 8/1979 | Kuriyama et al. | 210/616 |
| 4,184,946 | 1/1980 | Kato | 210/615 |
| 4,419,243 | 12/1983 | Atkinson et al. | 210/618 |

Primary Examiner—Thomas Wyse
Attorney, Agent, or Firm—LeBlanc, Nolan, Shur & Nies

[57] ABSTRACT

This invention provides a process and apparatus for the growth of biomass from a supply of suitable nutrient wherein the volume of biomass and the size and shape of the units in which it is present within a vessel (10) in which the reaction takes place can be accurately controlled. Control is achieved by providing a support structure (14) for the biomass comprising one or more movable bodies each of which has an internal reticular structure defining a substantial voidage therein and which essentially fills with the biomass but which does not overfill since excess growth is restricted. Restriction can be achieved by removal of excess biomass or by removal of the bodies at the time that they become filled. The techniques are capable of numerous industrial applications including various biological fermentation processes as well as the purification of sewage and industrial effluents, for example.

4 Claims, 4 Drawing Figures

GROWTH OF BIOMASS

This is a continuation of application Ser. No. 347,872, filed Feb. 11, 1982, now U.S. Pat. No. 4,419,243, which is a continuation-in-part of application Ser. No. 156,038, filed June 3, 1980, abandoned, which is a division of application Ser. No. 945,869 filed Sept. 26, 1978, abandoned.

This invention concerns a process wherein biomass is grown from a supply of suitable nutrient.

Examples of processes with which the invention is concerned and which are practised industrially are biological fermentation processes of various kinds and the treatment of sewage or industrial effluent by the so-called activated sludge process to reduce the BOD of the effluent.

The present invention is based upon an appreciation of the possibility of providing biomass within a reaction vessel such that the volume of biomass present is accurately known and is present in packages of known size and form. In this way the concentration of biomass can be sustained at an optimum level and the age of the biomass and therefore the overall yield from reactions, as well as the nature of those reactions themselves, can be determined and controlled.

According to the present invention, there is provided a process wherein biomass is grown from a supply of suitable nutrient material, comprising the steps of providing a vessel in which is contained a biomass support medium in the form of at least one movable body having an internal substantially uniform reticular structure defining an internal voidage consisting of a multiplicity of inter-connected pores such as to provide therein a protective environment which will permit biomass growth therewithin and thus support and contain biomass as a substantially integral mass within said voidage, the protective environment thus provided allowing the or each body to essentially fill with biomass over a period of time, there being an extensive area of access from the external surface of the or each said body to the whole of the voidage therein; causing the nutrient and any additional substances required for the process to contact and enter the support medium within the vessel; and causing movement of the support medium within the vessel during the growth process sufficiently for restricting accumulation of biomass outwardly from the outer surface of the or each said body and thus preventing overfill of biomass onto the outer surface of the or each said body.

The restriction of such outward accumulation can be achieved by continual or periodic removal of such biomass or by removal of the body or bodies from the vessel before such outward growth occurs.

Preferably the voidage within the internal structure of each said body is such that the biomass supported by and contained within said body is present as an integral mass.

In one preferred form of apparatus for carrying out the process there is provided a reaction vessel which contains a multiplicity of said bodies, each of which:

(a) is of such shape as to enable the bodies to move relative to one another with a rubbing and/or knocking action without packing together as a solid unit;

(b) has an outer surface of such character that the bodies do not interlock with one another during such relative movement;

(c) has substantial voidage within its internal structure; and (d) has an extensive area of access from its outer surface to such voidage.

The apparatus further includes means for passing fluid containing the nutrient material and other substances necessary to support the reaction through the vessel under such conditions that there is some movement of the individual bodies relative to one another such any biomass which tends to grow outwardly from the outer surfaces thereof is released through attrition.

In an alternative preferred form of apparatus for carrying out the process there is provided a reaction vessel containing a multiplicity of said bodies each of which:

(a) has an outer surface of such character that the bodies do not interlock with one another during relative movement;

(b) has substantial voidage within its internal structure; and (c) has an extensive area of access from its outer surface to such voidage;

The apparatus further includes means for introducing said bodies free or substantially free of biomass to the vessel and means for removing bodies supporting and substantially filled with biomass from the vessel, the residence time of bodies in the vessel being such that they are removed before growth of biomass outwardly from their outer surfaces can occur.

The invention will be further apparent from the following description with reference to the several figures of the accompanying drawings which show, by way of example only, two forms of apparatus for the treatment of sewage effluent by the so-called activated sludge treatment process and embodying the invention.

In the conventional activated sludge treatment process, sewage or industrial effluent is aerated and agitated within a vessel in the presence of a biological population which metabolises on various impurities contained within the effluent and grows to produce so-called secondary sludge which can be removed from the effluent by sedimentation. The concentration of biological population within the treatment vessel will vary with changes in composition of effluent, residence time and numerous other factors but will in any event be limited with the result that the treatment vessel will need to be much larger than would be necessary if higher concentrations of biological population could be sustained.

Figure 1:
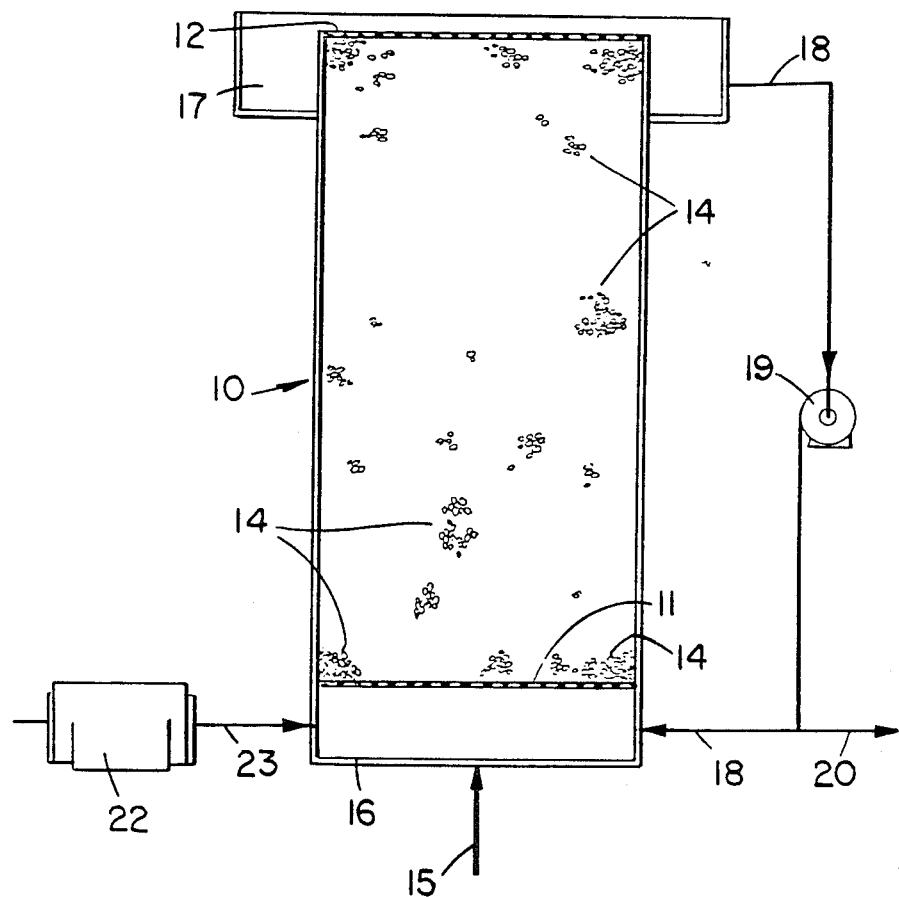
FIG. 1 shows a partially cut-away side elevation of the first form of apparatus.
Figure 3:
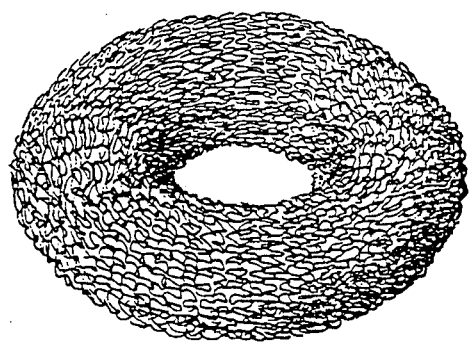
FIG. 3 shows a perspective view of one of the bodies of the apparatus of FIG. 1 or FIG. 2 and on an enlarged scale.

Referring now to FIGS. 1 and 3 of the drawings, it will be seen that the first form of apparatus is essentially comprised by a vertically extending cylindrical column forming a reaction vessel generally indicated at 10. The vessel 10 is closed adjacent its lower and upper ends by perforate plates 11 and 12 respectively. The space between the plates 11 and 12 is partially filled with a multiplicity of bodies 14 whose structure will be described in greater detail hereinafter. Each of the bodies 14 however supports and contains biomass forming part of the total biological population contained within the vessel 10.

Effluent, in this case sewage effluent derived from raw sewage after screening and, if required, primary sedimentation thereof, is passed upwardly through the vessel 10 by introduction through the line 15 to a chamber 16 located beneath the plate 11. Liquid leaves the upper end of the vessel 10 by passage through the apertures in the plate 12 to overflow into a collecting main or gutter 17 which is connected by a line 18 to the chamber 16 by way of a pump 19 which serves to recycle a portion of the liquid, excess liquid (equal to the inflow through line 15) being led away through the line 20 on the pressure side of the pump 19.

Air is supplied separately to the chamber 16 from a compressor 22 via a line 23.

As the effluent and air flow upwardly through the vessel 10 they react with the biological population supported and contained with the bodies 14 causing breakdown of various substances including carbonaceous and proteinaceous materials to produce carbon dioxide and additional biomass.

The bodies 14 do not pack the space between the plates 11 and 12 tightly, whereby the flow of gas and liquid through the vessel 10 causes some movement of the bodies 14 relative to one another within the bed. This movement is such as to cause the outer surfaces of the bodies 14 to rub and/or knock against one another, thus causing them to shed through attrition any excess biomass which tends to build up on their outer surfaces. Contact of the bodies with the walls of the vessel 10 and the flow of liquid over the bodies can also contribute to the release of excess biomass.

We have found that the concentration of biomass per unit volume of the reaction vessel utilising bodies of the kind with which we are here concerned can be greater by a factor of up to 5 than the concentration of biomass in a conventional aeration tank with the result that the capacity of the treatment vessel for a given through flow of effluent can be approximately 1/5 of that of the conventional vessel with a consequent and substantial reduction in the capital cost of a treatment plant, assuming equal biomass activity in both situations.

The bodies 14 are of special construction. Their overall shape is preferably generally rounded or sufficiently so to enable them to move relative to each other with a rubbing and/or knocking action without packing together as a solid unit. Again, the outer surfaces of the bodies are of such character that they do not interlock with one another during such relative movement. Each of the bodies has an internal, substantially uniform reticular structure throughout the entire volume of the body, defining an internal voidage consisting of a multiplicity of interconnected pores making up a continuous voidage. The average pore size which is substantially constant throughout is in the region of 0.3 mm to 1 mm in diameter, and optimum results are achieved at or close to 0.8 mm diameter. Thus their bulk density in air is substantially less than the density of the material from which they are formed. Each body has an extensive area of access to said voidage from its outer surface as by way of a multiplicity of said pores which are exposed at said surface. The internal voidage provides a protective environment which will permit biomass growth therewithin, and the volume of biomass supported and contained by each body is generally present as an integral mass or monolithic structure reinforced by the reticule within the body, and filling the body.

The bodies can be made from metal such as stainless steel, certain synthetic plastics, glass or other non-corrodible materials. The bodies may be substantially rigid or of sponge-like construction as provided by reticular foam which has been blown during production to remove the cell walls, leaving only a filamentous structure.

Various modifications are possible. For example, the reaction vessel may contain bodies of different size which will classify within the bed. Such different sized bodies might support different kinds of organism whereby different kinds of reaction may take place in the reaction vessel simultaneously.

Figure 2:
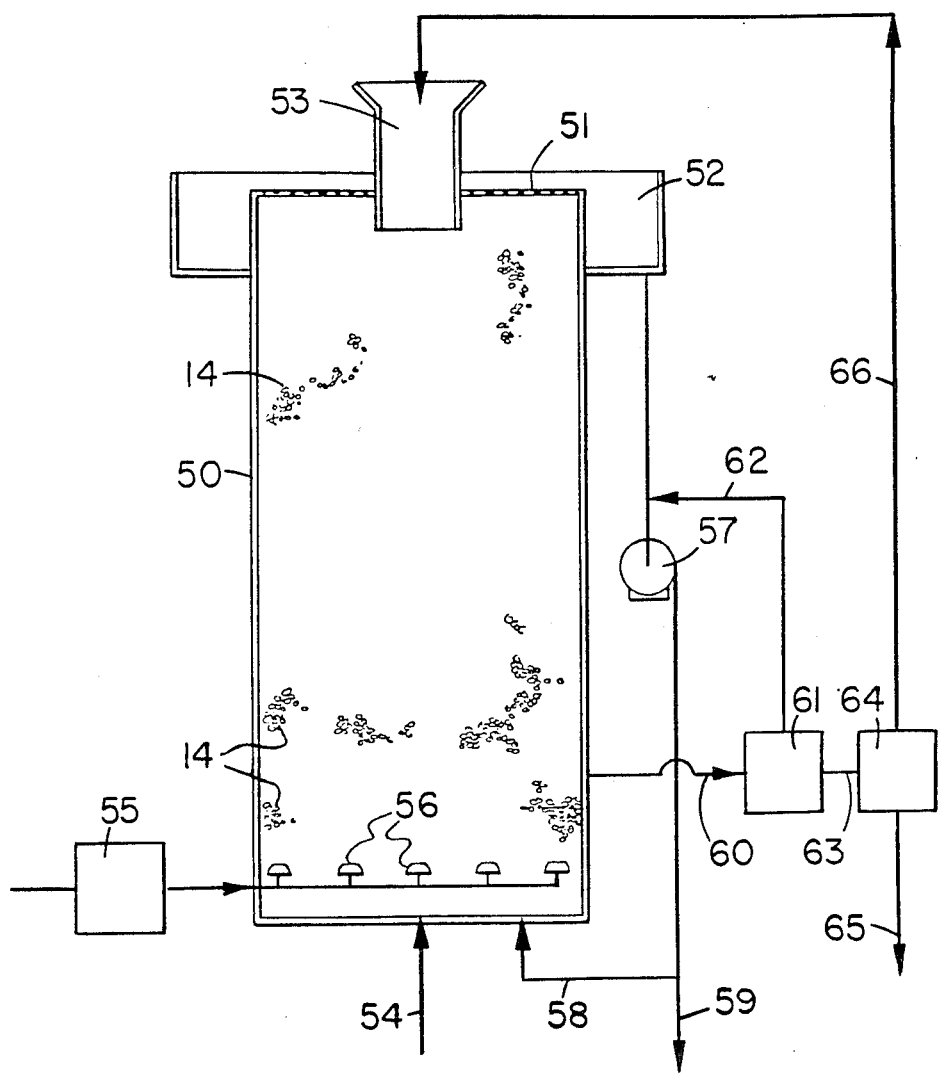
FIG. 2 shows a partially cut-away side elevation of the second form of apparatus.

Referring now to FIGS. 2 and 3 of the drawings, it will be seen that the second form of apparatus is essentially comprised by a vertically extending cylindrical column forming a reaction vessel generally indicated at 50. The upper end of the vessel 50 is closed by a perforate plate 51 and surrounded by a collecting main or gutter 52 whose function will be apparent hereinafter.

The vessel 50 contains a multiplicity of bodies 14, each of which is adapted to support and contain biomass forming part of the biological population contained within the vessel 50. The bodies 14 are similar to those described in connection with the apparatus of FIG. 1, and formed from a material which is less dense than water.

A duct 53 communicates with the interior of the vessel 50 adjacent its upper end, and serves to supply the bodies 14, free of biomass or substantially so, into the vessel 50.

Sewage effluent derived from raw sewage after screening, and, if required, primary sedimentation is introduced into the base of the vessel 50 through a line 54 together with air which is supplied from a compressor 55 into the vessel by way of diffusers 56.

As the effluent liquor and air pass upwardly through the vessel 50 various impurities, such as carbonaceous and proteinaceous material, contained within the effluent liquor, are metabolised by the biological population contained within the vessel 50.

The effluent liquor leaves the top of the vessel 50 through the perforations in the plate 51 to be collected in the main or gutter 52. The majority of the liquor flowing into the main or gutter 52 is recycled by means of a pump 57 to a line 58 for reintroduction to the vessel 50 at the base thereof. A smaller portion, equal to the feed through the line 54 is led off for further treatment through line 59.

Bodies 14 are removed from the vessel adjacent the base thereof through line 60 together with some of the effluent liquor. The mixture of bodies 14 and effluent liquor are passed to a straining device 61 which passes the liquor through line 62 to the suction side of the pump 57 and the separated bodies through line 63 to a machine 64 which separates biomass supported by and contained within the bodies from the bodies themselves. The separated biomass is removed through line 65 as secondary sludge, whilst the bodies 14 freed of biomass are passed through line 66 for supply to the duct 53.

It will be understood that the bodies are continuously recycled through the vessel 50. As the bodies 14 move downwardly through the vessel they gradually support and contain progressively more biomass, either becoming seeded with biomass contained within the recycling effluent liquor or being seeded by virtue of incomplete removal of biomass in the machine 64.

The apparatus is designed so that the residence time of the bodies within the vessel 50 is such that they are removed when they are substantially filled with biomass but before biomass can commence to grow outwardly from their outer surfaces.

The machine 64 may separate biomass from the bodies 14 by compression, intense vibration or other mechanical method. As an alternative, the bodies 14 may be freed of biomass for re-use, by a chemical or biological method such as extended aeration, for example.

The flow of liquor and air through the vessel 50 is such as to fluidise the bed of bodies 14 sufficiently to enable the bodies 14 to classify within the bed so that the apparatus operates in the manner described.

As with the first form of apparatus described, the concentration of biomass per unit volume of reaction vessel can be significantly greater than possible with conventional activated sludge processes.

Furthermore, the surplus recovered biomass will contain a smaller proportion of free (that is to say extracellular) water than conventional secondary sludges rendering dewatering to a combustible state more easy.

Various modifications are possible.

Thus, for example, if the bodies are made from a non-combustible material the biomass contained therein may be removed by combustion. Equally if the bodies are formed from a combustible material they may be burned with the included biomass, fresh bodies being supplied continually instead of recycling a given quantity thereof.

Again, for example, the bodies may be formed from a material more dense than water and passed through the vessel in the opposite direction, that is from bottom to top.

It will be understood that in both forms of apparatus described the quantity of biomass present in the reaction vessel at any time is reasonably accurately known as is the size and shape of the units or packages in which it is present and that control of the reaction can thus be more precise and predictable than has been possible hitherto with conventional apparatus.

Various interesting possibilities exist. For example, in either of the forms of apparatus described the bodies may be of such size that a sufficiently large volume of biomass is supported and contained whereby essentially aerobic processes take place at the surface of each body and within an internal layer adjacent such surface whilst essentially anaerobic processes such as the conversion of nitrates to nitrogen gas occur in the interior of the body in the deeper layers of biomass.

It must be understood that the size of body necessary to ensure that both aerobic and anaerobic processes take place will be dependent upon the dissolved oxygen level within the reaction vessel. It follows that the size of the body can be selected for a given dissolved oxygen level or the dissolved oxygen level can be adjusted for a given body size to give the desired level of both aerobic and anaerobic processes. Normally the desired level will be that which minimises biomass production.

As an alternative to bodies constructed from foamed plastics, one suitable body for use in the apparatus described with reference to either FIG. 1 or FIG. 2 is as illustrated in FIG. 3 and may be made from a single length of plastic monofilament which is knitted to form a piece of fabric in the form of a cylindrical tube which is then rolled into toroidal shape. In a typical example the toroid will have a diameter of 5 cm or thereabouts and a thickness of 2 cm or thereabouts.

This body is easily mass-produced and inexpensive and therefore attractive in applications where large quantities are required as, for example, in the treatment of sewage or industrial effluent.

Figure 4:
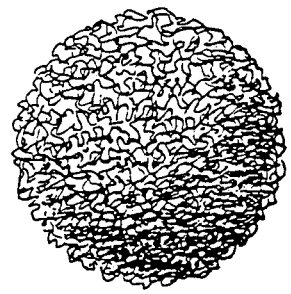
FIG. 4 shows a perspective view of an alternative form of body for the apparatus of FIG. 1 or FIG. 2, again on an enlarged scale.

Another suitable body is as shown in FIG. 4 and may be made from a single length of stainless steel wire which is knitted, again to form a cylindrical tube, a length of which is compressed into a generally spherical form. This body is relatively expensive but is more suitable for applications where bodies of smaller size having a diameter of 0.6 cm, for example, are required. Bodies made from stainless steel may be of particular interest where fine chemicals such as pharmaceuticals are to be produced.

It will be appreciated that it is not intended to limit the invention to the above examples only, many variations, such as might readily occur to one skilled in the art, being possible without departing from the scope thereof.

For example, instead of providing the bodies within a static vessel through which the materials to be treated are passed, the bodies may be contained within an open cage-like vessel which is itself moved through the materials to be treated. Such a cage-like vessel might take the form of a rotatable drum which is at least partially immersed in a body of liquid containing materials to be reacted.

Yet again, for example, the bodies may be contained within an open tank-like vessel which is continually stirred with sufficient vigour to cause the bodies to shed excess biomass through liquid shear or by attrition resulting from collision.

Whilst the necessary nutrients will normally be passed over the support structure for the biomass, in the form of a liquid together with such gaseous additives as may be necessary to support the required reactions, there may be applications where the necessary nutrients can be present in gaseous, mist or vapour form together with sufficient moisture to sustain the biological reaction.

Whilst we have described the invention with reference to the treatment of effluents, it will be understood that the techniques are applicable to any process wherein biomass is grown from a source of nutrient. Thus the techniques may be applied to the production of pharmaceutical substances and single cell proteins such as yeast. It is envisaged, for example, that fermenters used in the brewing and related industries might usefully contain the necessary yeast within bodies of the general kind which we have described.

It will be understood that the bodies, even whilst empty, may serve to act as a filter in the apparatus described with reference to FIG. 2 and in some applications such filtration effect may be advantageous.

What is claimed is:

1. A process for promoting the growth of biomass from a supply of suitable nutrient material, comprising the steps of providing a vessel in which is contained a biomass support medium in the form of a plurality of movable bodies each having a substantially uniform reticular structure throughout the entire volume of the body, defining an internal voidage consisting of a multiplicity of interconnected pores such as to provide throughout the body a protective environment which will permit biomass growth in said pores and thus support and sustain active biomass as a substantially integral mass retained by said reticular structure, said protective environment thereby allowing each body to fill with biomass over a period of time, there being an extensive area of access by way of a multiplicity of openings defined by said reticular structure at the external surface of each said body, to the whole of the voidage therein, the overall shape and reticular structure of each body being sufficiently plain as to enable the bodies to move relative to each other with a rubbing or knocking action without interlocking or packing together as a solid unit; causing the nutrient and any additional substances required for the process to flow through the vessel thus to contact and enter the bodies within the vessel; and causing relative movement of the bodies within the vessel during the growth process sufficiently for restricting accumulation of biomass outwardly from the outer surface of each said body and thus preventing overfill of biomass onto the external surface of each said body.

2. A process according to claim 1, wherein a gaseous medium is caused to flow over the bodies within the vessel.

3. A process according to claim 1, wherein the nutrient material is industrial or sewage effluent, and oxygen is introduced into the interior of the vessel to meet the biological oxygen demand.

4. A process according to claim 1, wherein bodies are removed from the vessel during the growth process and wherein the biomass contained within the bodies removed from the vessel is removed therefrom, and the bodies, substantially freed of biomass, are thereafter returned to the vessel.

* * * * *